United States Patent [19]

Gaylord, Jr.

[11] 4,205,667
[45] Jun. 3, 1980

[54] CERVICAL COLLAR

[75] Inventor: John F. Gaylord, Jr., Matthews, N.C.

[73] Assignee: Medical Specialties, Inc., Charlotte, N.C.

[21] Appl. No.: 893,405

[22] Filed: Apr. 4, 1978

[51] Int. Cl.² ............................................. A61M 1/02
[52] U.S. Cl. .................................. 128/75; 128/24 R; 128/DIG. 23
[58] Field of Search ................ 128/DIG. 23, 75, 24 R

[56] References Cited

U.S. PATENT DOCUMENTS

| | | | |
|---|---|---|---|
| 1,473,506 | 11/1923 | Nessler | 128/DIG. 23 |
| 3,008,464 | 11/1961 | Atkins | 128/14 R |
| 3,042,026 | 7/1962 | Monfardini | 128/75 |
| 3,374,785 | 3/1968 | Gaylord, Jr. | 128/75 |
| 3,612,046 | 10/1971 | Gaylor, Jr. | 128/75 |
| 3,696,810 | 10/1972 | Gaylord, Jr. | 128/75 |
| 3,756,226 | 9/1973 | Calabrese | 128/75 |
| 3,780,731 | 12/1973 | Quello | 128/75 |
| 3,964,474 | 6/1976 | Fox | 128/DIG. 23 |
| 3,992,238 | 11/1976 | Johns | 156/93 |
| 4,043,325 | 8/1977 | Ochs et al. | 128/87 B |

FOREIGN PATENT DOCUMENTS 2404683 7/1975 Fed. Rep. of Germany ............ 128/75

OTHER PUBLICATIONS

Catalog, Richards Mfg. Co., 4/1/66, p. 6-A.

Primary Examiner—Robert W. Michell
Assistant Examiner—J. L. Kruter
Attorney, Agent, or Firm—Bell, Seltzer, Park & Gibson

[57] ABSTRACT

A two part cervical collar which comprises a pair of U-shaped body members which are adapted to be positioned in a mating face-to-face arrangement encircling the neck of the wearer, with the oppositely directed end portions of the members over-lapping each other. Each body member comprises a core of air permeable foam material having sufficient firmness to provide adequate support about the entire circumference of the wearer's head and neck. The core of each body member defines a smooth exterior surface which is in the form of a portion of a cylindrical surface, and the core is covered by a fabric which is smoothly bonded to the surface thereof. Also, strap means having Velcro type hook fastening means thereon is provided for releasably interconnecting the two mating members.

11 Claims, 13 Drawing Figures

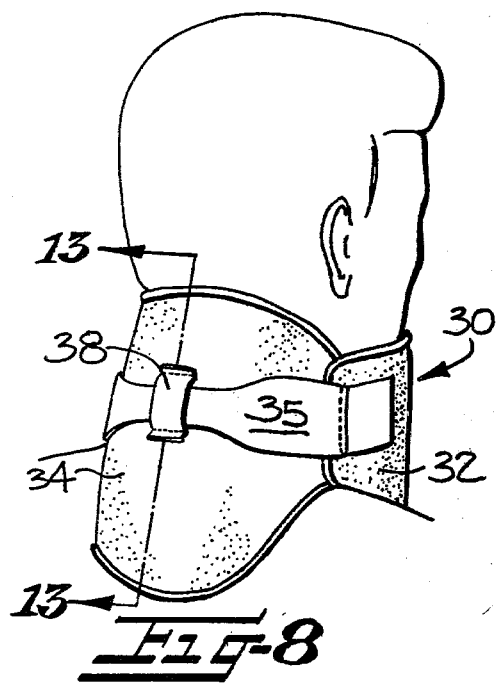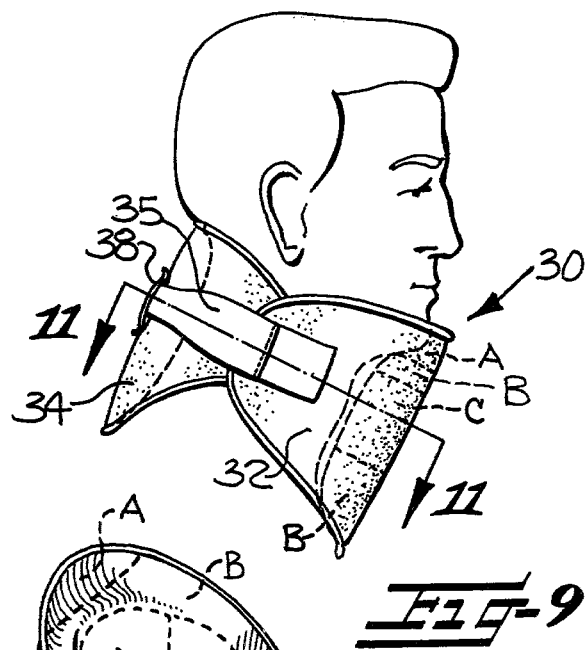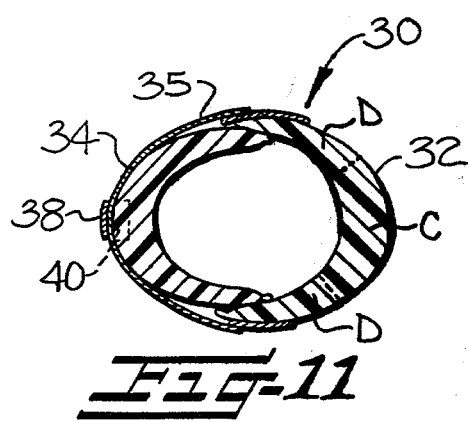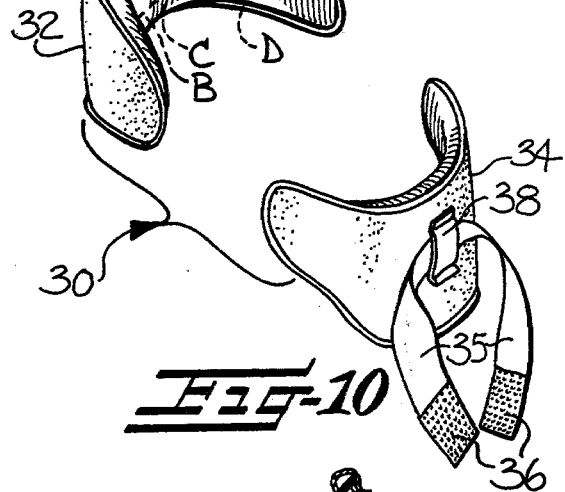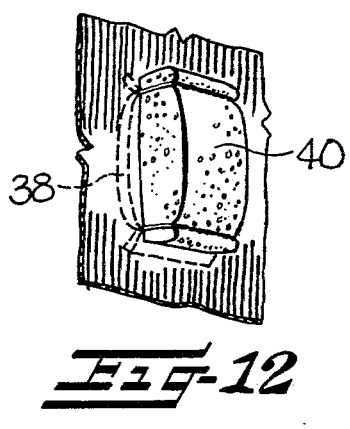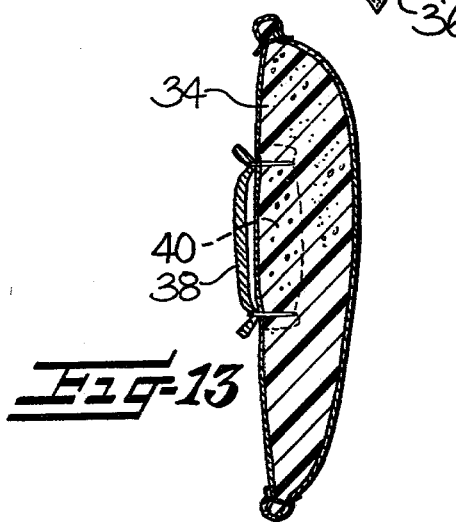

CERVICAL COLLAR

The present invention relates to a novel two part cervical collar useful in the treatment of various neck injuries and pathological disorders.

Cervical collars of various designs are well-known in the medical art, including the one piece collars designed to closely surround the neck and as described in the applicant's prior U.S. Pat. Nos. 3,374,785 and 3,696,810. There has also been marketed a cervical collar of the type described in U.S. Pat. No. 3,756,226 to Calabrese et al, and which comprises two mating halves which are adapted to be positioned to encircle, but remain somewhat spaced from, the wearer's neck. More particularly, the front half of the Calabrese collar is adapted to extend between the sternum and chin and the rear half is adapted to extend between the upper back and the occipital region of the head. The collar is formed from a very lightweight foam material, and a rigid brace is positioned at the medial portion of the front half to support the chin, and a second brace is positioned in the medial portion of the rear half to support the occipital region.

While the Calabrese collar provides adequate support in the forward and rear plane, it provides inadequate support in the two lateral directions, thereby permitting the wearer's head to tilt to the sides to an undesirable degree. Further, the rigid braces concentrate the support forces and tend to bite into the wearer's body after prolonged use, and the presence of the rigid brace along the rear half of the collar renders it uncomfortable for the wearer to lie down with the collar in place, since the rear brace precludes free rolling movement of the collar on the bed.

It is accordingly an object of the present invention to provide a two part cervical collar of the described type and which provides firm support about the entire circumference of the wearer's head and neck.

It is also an object of the present invention to provide a two part cervical collar which is comfortable to wear, and wherein the exterior surface of at least the rear half comprises a smooth, substantially uninterrupted, cylindrical surface which is adapted to provide free rolling contact with a bed when the wearer is lying down.

It is a further object of the present invention to provide a two part cervical collar which remains somewhat spaced from the neck in use to facilitate its comfort, and is fabricated from a relatively stiff and firm foam material which has sufficient air permeability to permit ventilating air circulation therethrough.

It is another object of the present invention to provide a two part cervical collar wherein the positioning of the wearer's head and neck, and in particular the degree of flexure and hypertension, can be adjusted by interchanging collar halves of varying size.

These and other objects and advantages of the present invention are achieved in the embodiments illustrated herein by the provision of a cervical collar which comprises a pair of U-shaped body members which are adapted to be positioned in a mating face-to-face arrangement encircling the neck of the wearer, with the oppositely directed end portions overlapping each other. Each of the body members comprises a core of resilient foam material having a density of between about four to ten pounds per cubic foot and sufficient firmness to provide adequate support about the entire circumference of the wearer's head and neck. A fabric covers the core, and both the core and fabric are relatively air permeable to facilitate the passage of ventilating air therethrough. The collar also includes fastening means for releasably securing the two body members in their mating face-to-face arrangement.

The exterior surface of both body members preferably conforms to a portion of a right cylindrical surface, which is relatively smooth and uninterrupted, to facilitate free rolling movement of the collar on a bed. Also, the fabric is preferably smoothly bonded to the adjacent surface of the core throughout the full area thereof, to thus enhance the appearance of the collar.

Some of the objects having been stated, other objects and advantages will appear as the description proceeds, when taken in connection with the accompanying drawings, in which—

FIG. 8 is a perspective view of a second embodiment of a cervical collar embodying the present invention and operatively positioned about a wearer's neck;

FIG. 9 is a side elevation view of the collar shown in FIG. 8;

FIG. 10 is a perspective view of the two halves of the collar of FIG. 8 in disassembled relationship;

FIG. 11 is a sectional plan view taken substantially along the line 11—11 of FIG. 9;

FIG. 12 is a fragmentary perspective view illustrating the procedure and structure by which a flap is mounted to the exterior surface of the rear body member; and FIG. 13 is a vertical sectional view taken substantially along the line 13—13 of FIG. 8.

Figure 1:
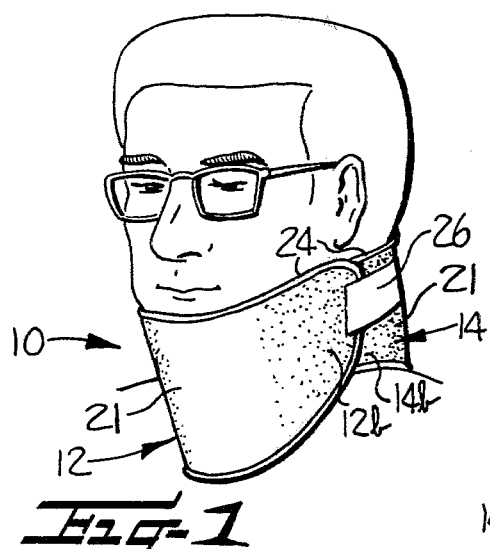
FIG. 1 is a perspective view showing a cervical collar embodying one embodiment of the present invention and operatively positioned about a wearer's neck.
Figure 2:
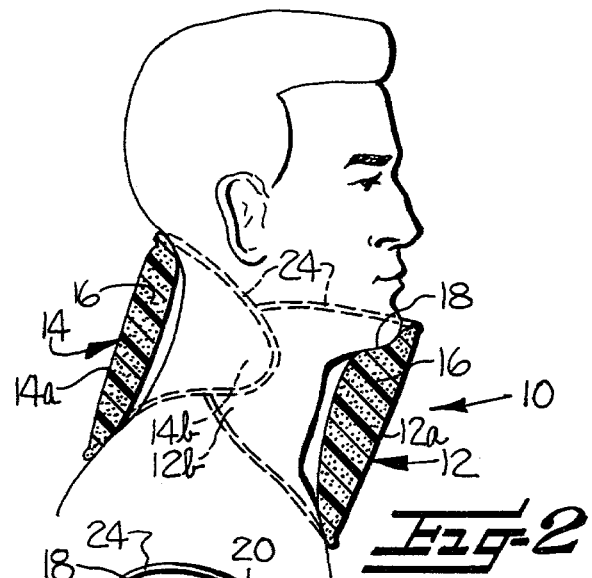
FIG. 2 is a side elevation view of the cervical collar operatively positioned about a wearer's neck, with the collar being illustrated in vertical section.
Figure 3:
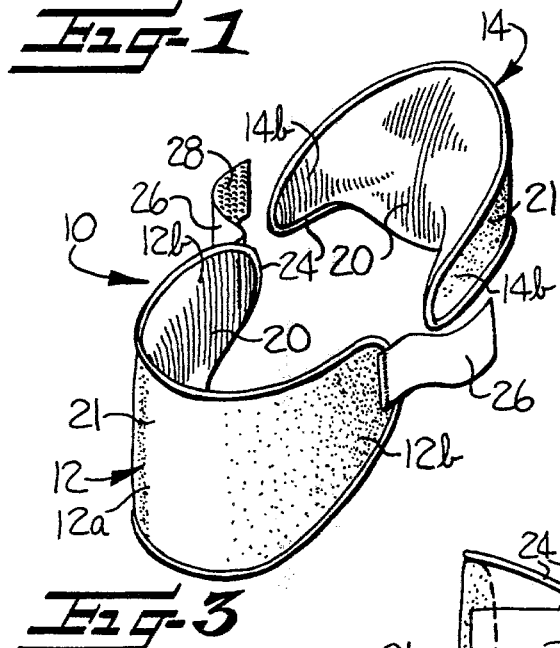
FIG. 3 is a perspective view of the two halves of the collar in disassembled relationship.
Figure 4:
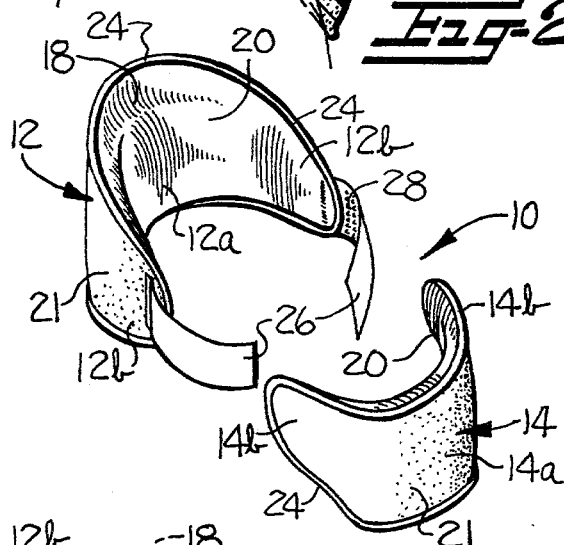
FIG. 4 is a view similar to FIG. 3, but illustrating the disassembled collar from an opposite direction.
Figure 5:
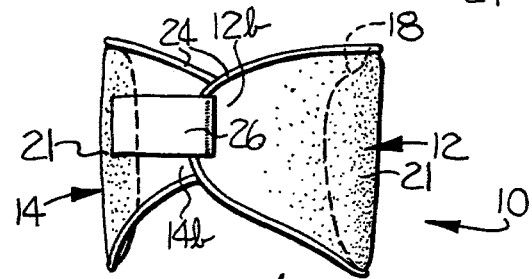
FIG. 5 is a side elevation view of the collar in assembled relationship.

Referring more particularly to the drawings, the numeral 10 broadly indicates the embodiment of the cervical collar shown in FIGS. 1–7, and which comprises a front U-shaped body member 12 and a rear U-shaped body member 14. Each body member comprises a medial portion at 12a, 14a, respectively, and two end portions 12b and 14b, respectively. The two members 12 and 14 are adapted to be positioned in a mating face-to-face arrangement encircling the neck of the wearer, with the oppositely directed end portions overlapping each other, note for example FIGS. 6 and 7. Typically, the width of each body member at its medial portion is about twice the width at its end portions, note for example FIG. 5. In the operative position of the collar, the medial portion 12a of the front body member 12 extends between the chin and sternum of the wearer and is somewhat spaced from the neck, and the medial portion 14a of the rear body member extends between the upper back and occipital region, and is somewhat spaced from the back of the neck. This spaced relationship improves the comfort of the collar by facilitating cooling air flow, and permits the collar to be worn over bandages, a cast, or the like. Also, the fact that the collar contacts the head and body of the wearer along a relatively large circle results in improved stability as compared to a collar which closely surrounds the neck.

Each of the body members 12 and 14 further comprises a relatively firm and air permeable core 16 of resilient foam material. More particularly, the foam core 16 is of sufficient firmness to provide adequate support about the entire circumference of the wearer's head and neck without the use of additional rigidifying members. Preferably, the core 16 comprises myriad discrete particles of foam which are bonded together with a suitable binder during a molding operation as hereinafter further described, and with the core having a density of between about four to ten pounds per cubic foot. Also, the core is sufficiently porous to permit the passage of ventilating air therethrough, thereby further contributing to the comfort of the wearer during extended periods of use.

Figure 6:
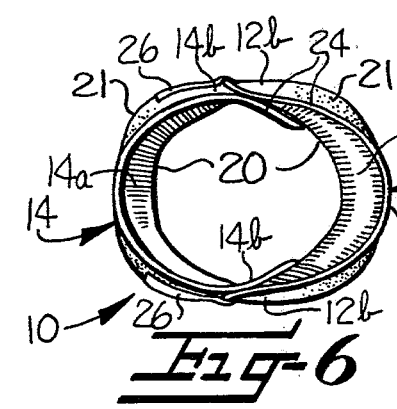
FIG. 6 is a top plan view of the collar in assembled relationship.
Figure 7:
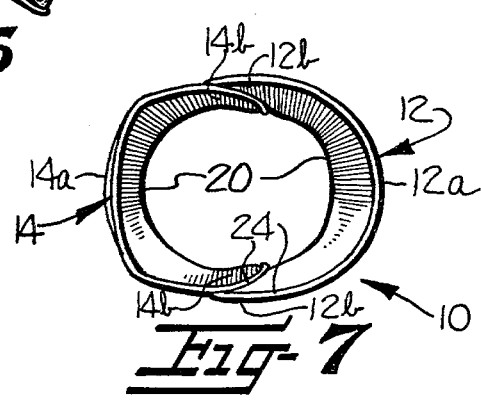
FIG. 7 is a bottom plan view of the collar in assembled relationship.

As best seen in FIGS. 6-7, the exterior surface of the core of each of the two body members generally conforms to a portion of a right cylindrical surface, which is relatively smooth and uninterrupted by the presence of any extraneous rigidifying members or other components. The inner surface of each body member is also smooth and uninterrupted, and is somewhat convex in vertical cross-section (note FIG. 2) such that the central portion is more thick than are the upper and lower edge portions. Still further, the thickness of the core 16 in each body member tapers from a maximum thickness at its medial portion to a reduced thickness adjacent each end portion, note FIGS. 6 and 7. The front body member 12 includes an indentation 18 in the inner surface which extends along the upper edge portion thereof for receiving and supporting the chin of the wearer.

The inner and outer surfaces of the core 16 of each body member are covered by sheets 20, 21 respectively, of a suitable fabric, and a narrow seam binding strip 24 or tape is stitched along the upper and lower edges to cover and secure the raw edges of the two sheets of the fabric. The fabric employed in the two sheets is preferably resilient, and is smoothly bonded to the core in conforming relationship to the curved surfaces thereof to provide a neat, non-baggy appearance, even when the body member is deformed or flexed. Stretch fabrics are particularly suitable by reason of their ability to conform to the shape of the core. Also, the fabric of the outer sheet 21 may be napped for the purposes to become apparent. As particular examples, the fabric 20 may comprise a knitted 100/2 ply stretch nylon, and the fabric 21 may comprise a similar material but with the outer surface being lightly napped.

The collar 10 further comprises means for releasably securing the two body members in their operative, mating face-to-face arrangement. As illustrated, this fastening means comprises a flexible strap 26 mounted to each end portion 12b of the front body member and extending circumferentially therefrom. The inner surface of each strap 26 includes Velcro type hook means 28 which is adapted to releasably engage the raised fibers of the napped outer sheet 21 of the rear body member 14. Thus the two body members may be interconnected after being properly positioned about the neck of the wearer, by simply pressing the straps 26 against the outer surface of the rear member 14, and subsequently disconnected by simply peeling the straps from the rear member.

A second embodiment of a cervical collar embodying the present invention is illustrated generally at 30 in FIGS. 8-13. The collar 30 comprises front and rear body members 32 and 34 respectively, which are generally similar in structure to the above-described body members 12 and 14. However, the collar 30 includes a fastening means which is more readily reachable from the front of the wearer, as opposed to the fastening means of the collar 10 which is more readily reachable from the rear. More particularly, the fastening means of the collar 30 comprises a flexible strap 35 having a length sufficient to extend circumferentially along the outside surface of the rear body member 34 and extend beyond the end portions thereof. Velcro type hook means 36 is mounted to each end of the strap for releasably engaging the napped fabric of the front body member 32.

The strap 35 is attached to the medial portion of the rear body member 34 by means of a flap 38 which is mounted to the exterior surface to form a loop thereon, and with the strap 35 being slideably mounted through the loop. The flap 38 is secured to the body member 34 by a procedure wherein the flap is initially secured by stitching to the fabric prior to the molding of the core, and with a foam block 40 being also secured to the opposite face of the fabric to better support the flap, note FIG. 12. The block 40 is then integrally molded into the core as further described below and as illustrated in FIG. 13.

In order to permit the collars 10 and 30 to provide adequate support, without unduly increasing its bulk and restricting its porosity, it is advantageous to vary the density of the core of each body member in a predetermined manner. For example, the density preferably is relatively high along the thin upper and lower edge portions to insure adequate firmness, and the density is relatively low at a point midway between the upper and lower edge portions to maximize air permeability. As a particular example, the portion of the collar illustrated at A in FIGS. 9 and 10 may have a density of about 9½ pounds per cubic foot, the portion at B a density of about 6½ pounds per cubic foot, the portion at C a density of about 4½ pounds per cubic foot, and the portion at D a density of about 5 pounds per cubic foot.

In fabricating the body members of the collars 10 and 30, it is advantageous to mold the foam core while simultaneously applying and bonding the sheets of covering fabric thereto. A molding apparatus is preferably employed which has a cooperating pair of male and female molding dies of suitable shape for forming the core into the desired configuration. Initially, common or virgin foam, such as polyurethane, is shredded or otherwise formed into discrete particles, and the particles are thereafter mixed with a binder in a ratio of about ten to one by weight, and heated to form a tacky mass. Suitable binders are well known in the art, and a typical example is a long chain polyether polyol, with tolylene diisocyanate. The sheets of covering fabric are then positioned to overlie each of the male and female molding dies, and in the case of the collar 30, the outer sheet of the rear body member will have the flap 38 and foam block 40 secured thereto as described above. The foam mass is next placed in the female molding die, and a vacuum may be drawn on the mass to maintain its position. The dies are then closed to form the mass into the desired configuration. In this regard, the density of the foam in various portions of the core may be controlled to achieve the above described density variations by the placement of predetermined amounts of the foam mass in the various portions of the female die. The foam mass is then cured, as by subjecting it to steam while the dies are closed, to form a resilient core of rebonded polyurethane foam, with the sheets lightly bonded to both surfaces thereof. The same binder which bonds the foam particles together thus serves to lightly and smoothly bond the sheets to the core without undesirably affecting the softness of the fabric sheets. To complete the manufacturing operation, the molded product is removed from the molding dies, and the binding strip 24 is sewn along the edges. In the case of the collar 10, the two connecting straps 26 are sewn to the end portions of selected products, while in the case of the collar 30, the strap 35 is inserted through the loop of the flap 38.

In the drawings and specification, there has been set forth a preferred embodiment of the invention, and although specific terms are employed, they are used in a generic and descriptive sense only and not for purposes of limitation.

That which is claimed:

1. A two part cervical collar adapted to encircle a wearer's head and neck to immobilize the same, and characterized by the ability to provide adequate support about the entire circumference of the head and neck, and comprising a pair of U-shaped body members each comprising a medial portion and opposite end portions, and which are adapted to be positioned in a mating face-to-face arrangement encircling the neck of the wearer with the oppositely directed end portions overlapping each other and with the medial portion of one of said body members extending between the chin and sternum of the wearer and the other body member extending between the upper back and occipital region of the wearer, the exterior surface of each of said body members generally conforming to a portion of a right cylindrical surface of a diameter to extend beyond the chin of the wearer when operatively disposed about the neck and being relatively smooth and uninterrupted, each of said body members further comprising a relatively air permeable core of myriad discrete particles of resilient foam material which are bonded together, said core having a density of between about four to ten pounds per cubic foot and sufficient firmness to provide adequate support about the entire circumference of wearer's head and neck, with the core of said one body member having sufficient thickness to form a relatively broad chin support within the circumference defined by the exterior surface of said one body member, and a relatively air permeable fabric overlying said core, said fabric comprising a resilient fabric material which is smoothly bonded to the adjacent surface of said core throughout the full area thereof, and fastening means for releasably securing said body members in said mating face-to-face arrangement, said fastening means comprising flexible strap means mounted to one of said body members, and hook means mounted on said strap means, and with said fabric material which overlies the outer surface of the other of said body members having a texture which is adapted to be releasably engaged by said hook means.

2. The cervical collar as defined in claim 1 wherein each of said body members has a width at its medial portion which is approximately twice the width at the end portions thereof.

3. The cervical collar as defined in claim 2 wherein each of said body members has an inner surface which is somewhat convex in vertical cross section such that the central portion is more thick than the upper and lower edge portions.

4. The cervical collar as defined in claim 3 wherein the thickness of said core of each body member tapers from a maximum thickness at said medial portion to a reduced thickness adjacent each end portion.

5. The cervical collar as defined in claim 1 wherein said fabric material which overlies the outer surface of the other of said body members has a napped outer surface to facilitate engagement by said hook means.

6. The cervical collar as defined in claim 1 wherein said flexible strap means comprises a flexible strap mounted to each end portion of said one body member and extending circumferentially therefrom, and with said hook means being mounted on each strap.

7. The cervical collar as defined in claim 1 wherein said flexible strap means comprises a flexible strap having a length sufficient to extend circumferentially along the outside surface of said one body member and extend beyond the end portions thereof, means attaching said strap to said one body member, and with said hook means mounted to each end of said strap.

8. The cervical collar as defined in claim 7 wherein said attaching means comprises a flap mounted to the exterior surface of said one body member to form a loop thereon, and with said strap being slideably mounted through said loop.

9. A two part cervical collar adapted to encircle a wearer's head and neck to immobilize the same, and characterized by the ability to provide adequate support about the entire circumference of the head and neck, and comprising a pair of U-shaped body members each comprising a medial portion and opposite end portions, and which are adapted to be positioned in a mating face-to-face arrangement encircling the neck of the wearer with the oppositely directed end portions overlapping each other and with the medial portion of one of said body members extending between the chin and sternum of the wearer and the medial portion of the other body member extending between the upper back and occipital region of the wearer, each of said body members further comprising a relatively firm and air permeable core of discrete particles of resilient foam material which are bonded together and having a density of between about four to ten pounds per cubic foot, said core having an exterior surface which generally conforms to a portion of a right cylindrical surface, and a relatively air permeable fabric smoothly bonded to said core throughout the full area thereof, and fastening means for releasably securing said body members in said mating face-to-face arrangement, said fastening means comprising flexible strap means mounted to one of said body members, and hook means mounted on said strap means, and with said fabric material which overlies the outer surface of the other of said body members having a texture which is adapted to be releasably engaged by said hook means.

10. The cervical collar as defined in claim 9 wherein each of said body members has an inner surface which is somewhat convex in vertical cross section, and wherein the thickness of said core of each body member tapers from a maximum thickness at its medial portion to a reduced thickness adjacent each end portion.

11. The cervical collar as defined in claim 10 wherein the density of said core varies in a predetermined manner, and is between about 6½ to 9½ pounds per cubic foot along the upper and lower edge portions and between about 4½ to 5 pounds per cubic foot midway between said upper and lower edge portions.

* * * * *